United States Patent [19]

Bigner et al.

[11] Patent Number: 5,558,852
[45] Date of Patent: Sep. 24, 1996

[54] METHODS OF TREATING MELANOMAS AND GLIOMAS WITH MONOCLONAL ANTIBODY ME1-14

[75] Inventors: Darell D. Bigner, Mebane, N.C.; Michael R. Zalutsky, Chaple Hill, N.C.

[73] Assignee: Duke University, Durham, N.C.

[21] Appl. No.: 339,582

[22] Filed: Nov. 14, 1994

Related U.S. Application Data

[63] Continuation of Ser. No. 33,864, Mar. 19, 1993, abandoned.

[51] Int. Cl.⁶ .................. A61K 39/395; A61K 39/44
[52] U.S. Cl. ............... 424/1.49; 424/133.1; 424/138.1; 424/155.1; 424/156.1
[58] Field of Search .................. 424/130.1, 133.1, 424/138.1, 141.1, 143.1, 152.1, 155.1, 156.1, 1.49

[56] References Cited

PUBLICATIONS

3M. Bourdon et al., *Cancer Research* 43, 2796–2805 (1983).
L. S. Lashford et al., *Cancer* 61, 857–868 (1988).
R. P. Moseley et al., *Br. J. Cancer* 62, 637–642 (1990).
R. P. Moseley et al., *Int. J. Cancer* 52, 38–43 (1992).
V. Papanastassiou et al., *J. Neurooncology* 12, 268 (1992).
P. Riva et al., *Nuclear Medicine Communications* 13, 635 (1992).
J. M. Schuster et al., *Cancer Research* 57, 4164–4169 (1991).
M. R. Zalutsky et al., *Cancer Research* 49, 5543–5549 (1989).
E. V. Colapinto et al., *Cancer Research* 50, 1722–1827 (1990).
Harris et al., TibTech 11:42–44 (1993).
Stoolman Cell 56: 907–910 (1989).
Zalutsky et al., Cancer Research 50:4105–4110 (1990).
Carrel et al., Acta Neuro Pathol. (Berl) 57:158–164 (1982).
Garg et al.; *Chemical Abstracts*, 117:336–337 (No. 247833k) (Dec. 1992).

*Primary Examiner*—Margaret Parr
*Assistant Examiner*—Phillip Gambel
*Attorney, Agent, or Firm*—Bell, Seltzer, Park & Gibson

[57] ABSTRACT

Methods of treating solid or cystic tumors are disclosed. The method comprises administering to a human subject afflicted with a tumor an antibody in a therapeutically effective amount, wherein the antibody is monoclonal antibody Me1-14 or an antibody which binds to the epitope bound by monoclonal antibody Me1-14, and wherein the Fc receptor of the antibody is deleted. When the tumor is a brain tumor, the antibody may be administered by intrathecal injection. If the brain tumor is a cystic brain tumor, and the administering step may be carried out by depositing the antibody in the cyst cavity of the cystic brain tumor. Particularly preferred is a monoclonal antibody Me1-14 F(ab')$_2$ fragment coupled to $^{131}$I.

28 Claims, 2 Drawing Sheets

```
      -20
       M  N  F  G  F  S  I  F  L  V  L  V  K  G
     CTTCTTATGAACTTCGGGTTCAGCTTGATTTTCCTTGTCCTTGTTTTAAAAGGTAATTTA
  1

TTGAAGAGATGACATCTATTTTACGCACATGAGACAGAAAAAATGTGGTTTGTTTTGT
 60
                                 G  V  Q  C  E  V  K  L
                                                     +1
     TAGTGACAGTTTTCCAACCAGTATTCTCTGTTTGTAGGTGTCCAGTGTGAAGTGAAGCTG
120
      V  E  S  G  G  G  L  V  K  P  G  G  S  L  K  L  S  C  A  A
                                                    -4
     GTGGAGTCTGGGGGAGGCTTAGTGAAGCCTGGAGGGTCCCTGAAACTCTCCTGTGCAGCC
180
      S  G  F  T  F  S  S  Y  A  M  S  W  V  R  Q  T  P  E  K  S
     TCTGGATTCACTTTCAGTAGCTATGCCATGTCTTGGGTTCGCCAGACTCCAGAGAAGAGC
240
      L  E  W  V  A  S  I  S  S  G  D  S  T  Y  Y  P  D  S  V  K
     CTGGAGTGGGTCGCATCCATTAGTAGTGGTGATAGCACCTACTATCCAGACAGTGTGAAG
300
      G  R  F  T  I  S  R  D  N  A  R  N  I  L  Y  L  Q  M  S  S
     GGCCGATTCACCATCTCCAGAGATAATGCCAGGAACATCCTCTACCTGCAAATGAGCAGT
360
      L  R  S  E  D  T  A  M  Y  Y  C  A  R  G  G  W  L  H  Y  F
     CTGAGGTCTGAGGACACGGCCATGTATTACTGTGCAAGAGGCGGATGGTTACACTACTTT
420
      D  Y  G  Q  G  T  L  T  V  S  S
     GACTACGGGGGCCAAGGCACCACTCTCACAGTCTCCTCA
480
```

FIG. 1A.

```
  1   ATATTCTACTGCCCCAGAGATTTAATAATCTGATCATACACACTCCAACAGTCATTCTTG
                                   -20    M  R  P  S  I  Q  F  L  G  L  L  F  L  W
 60   GTCAGGAGACGTTGTAGAAATGAGACCGTCTATTCAGTTCCTGGGGCTCTTGTTTGTTCTG
       L  H
120   GCTTCATGGTGTAAGGAGTTTAACATTGAATATGCTAAAAAAGAGTATGTGATCAGGAATTTC
                                                        +1    G  A  H  C  D  I  Q  M  T  Q  S  P  S  S  L  S  A
180   TGGTCCTTCAGAAAAATCTTTCTTTGAATATAATTAATTTCATAGGGACTTGTGTTCTTTT
       -4
             S  L  G  K  V  T  I  T  C  K  A  S  Q  D  I  N  K  Y  I
240   TAATTATAGGTGCTCACTGTGACATCCAGATGACACAGTCTCCATCCTCACTGTCTGCAT
       A  W  Y  Q  H  K  P  G  K  G  P  R  L  M  H  Y  T  S  T
300   CTCTGGGAGGCAAGGTCACCATCACTTGCAAGGCAAGTCAAGACATTAACAAGTATATAG
       L  Q  P  G  I  P  S  R  F  S  G  S  G  S  G  R  D  Y  S  F
360   CTTGGTATCAACACAAACCTGGAAAAGGTCCTAGGCTGATGCATTACACATCTACAT
       S  I  S  N  L  E  P  E  D  I  A  T  Y  Y  C  L  Q  Y  D  N
420   TACAGCCAGGCATCCCATCCCGATTCAGTGGCAGTGGATCTGGGACAGATTATTCCTTCA
       L  T  F  G  G  G  T  K  L  E  I  K  R  K
480   GCATCAGCAACCTGGAGCCTGAAGATATTGCAACTTATTGTCTACAGTATGATAATC
540   TTCTCACGTTCGGTGGAGGGACCAAGCTGGAAATAAAACGTAAGTAGTCTTCTCAACTT
```

FIG. 1B.

METHODS OF TREATING MELANOMAS AND GLIOMAS WITH MONOCLONAL ANTIBODY ME1-14

This invention was made with government support under grant numbers NS20023 from the National Institutes of Health, CA56115 from the National Institutes of Health, and CA42324 from the National Institutes of Health. The government has certain rights to this invention.

This is a continuation of application Ser. No. 08/033,864 filed on Mar. 19, 1993, now abandoned.

FIELD OF THE INVENTION

The present invention relates to the treatment of cancer in general, and particularly relates to the treatment of melanomas and gliomas of the central nervous system and treatment with the antibody ME1-14 F(ab')$_2$.

BACKGROUND OF THE INVENTION

Despite years of intensive investigation, the prognosis for most patients with anaplastic central nervous system (CNS) tumors remains poor. Median survival for adults with the most common form of CNS tumor, the glioblastoma multiforme, is 8–12 months. The outlook is somewhat better for less common tumors such as anaplastic astrocytoma and medulloblastoma, but most primary anaplastic CNS tumors are highly resistant to currently available therapy.

Only radiotherapy has been shown to prolong survival in patients with anaplastic gliomas. Following conventional therapy with surgery and external beam radiotherapy, malignant gliomas tend to recur at or near the original tumor site. Temporarily implanted radioactive iodine sources (interstitial brachytherapy) have recently been used to deliver high dose focal radiotherapy to locally recurrent malignant gliomas.

Radiotherapy is also utilized in the treatment of CNS melanoma. Response rates vary from 37% to 100%. The reported mean duration of response to palliative radiotherapy in CNS melanoma varies from 2 to 5 months, and mean survival following irradiation ranges from 2 to 7.6 months (average 3.8 months). No single treatment regimen has been shown to be superior in improving response rate and survival time. See Mastrangelo et al., *In Cancer: Principles and Practices of Oncology*, pp. 1403–1404 (DeVita, Hellman & Rosenberg Eds. 1985). Nevertheless, satisfactory treatments are not yet available for CNS cancers, and there is a continued need for new treatments for these diseases.

The possibility of using therapeutic antibodies to treat CNS neoplasms is beginning to be investigated. R. Moseley et al., *Br. J. Cancer* 62, 637 (1990) describe the intrathecal administration of $^{131}$I radiolabelled monoclonal antibody for the treatment of neoplastic meningitis.

The use of intact ME1-14 to treat three patients with CNS melanoma is described in L. Lashford et al., *Cancer* 61, 857 (1988), and Moseley et al., *Br. J. Cancer,* 62, 637 (1990).

The F(Ab')$_2$ fragment of Me1-14 also localized specifically in paired-label studies to human glioma xenografts in athymic mice and has been administered and shown to localize specifically and similarly in human gliomas in the brain of patients. See M. Zalutsky et al., *Cancer Res.,* 50, 4105, (1990); Behnke et al., *Brit. J. Neurosurg.* 2,193, (1988); Behnke et al., *In Brain Oncology—Biology, Diagnosis, and Therapy,* pp. 125–128 (Chatel et al., Eds. 1987).

Systemically administered $^{131}$I-labeled Me1-14 F(Ab')$_2$ to mice bearing intracerebral human D-54 MG xenografts is described in Colapinto et al., *Cancer Res.,* 50, 1822 (1990).

SUMMARY OF THE INVENTION

A first aspect of the present invention is a method of treating a tumor in a human subject. The method comprises administering to a human subject afflicted with a tumor (e.g., a brain tumor) an antibody in a therapeutically effective amount, wherein the antibody is monoclonal antibody Me1-14 or an antibody that binds to the epitope bound by monoclonal antibody Me1-14, and wherein the Fc fragment of the antibody is deleted. When the tumor is a brain tumor, the antibody may be administered by intrathecal injection. If the brain tumor is a cystic brain tumor, the administering step may be carried out by depositing the antibody in the cyst cavity of the cystic brain tumor.

Also disclosed is a method of treating a solid tumor in a human subject in need of such treatment. The method comprises removing a solid tumor from a solid tissue organ of an afflicted human subject, then forming an enclosed resection cavity in the solid tissue organ at the location from which the solid tumor was removed, and then administering to the subject an antibody in a therapeutically effective amount. The antibody is either monoclonal antibody Me1-14 or an antibody that binds to the epitope bound by monoclonal antibody Me1-14, and the Fc fragment of the antibody is deleted. The administering step is carried out by depositing the antibody in the resection cavity.

Also disclosed herein is the use of antibodies as described above for the preparation of a medicament for carrying out the methods of treatment as described above.

The foregoing and other objects and aspects of the present invention are explained in detail in the drawings herein and the specification set forth below.

BRIEF DESCRIPTION OF THE DRAWINGS

FIGS. 1A and 1B shows the nucleotide sequence and deduced amino acid sequence for the ME1-14 heavy (FIG. 1A) (SEQ ID NO:1 and SEQ ID NO:1, RESPECTIVELY) and light-chain (FIG. 1B) (SEQ ID NO:3 and SEQ ID NO:4 RESPECTIVELY) variable region genes. The nucleotide sequence is numbered in the left hand margin. The deduced amino acid sequence is above the nucleotide sequence. Superscript numbers above the amino acid sequence delineate the leader sequence (—20, –4) and the beginning of the actual immunoglobulin sequence (+1). Underlined amino acids match the sequence obtained from N-terminal amino acid sequencing.

DETAILED DESCRIPTION OF THE INVENTION

Amino acid sequences disclosed herein are presented in the amino to carboxy direction, from left to right. The amino and carboxy groups are not presented in the sequence.

Nucleotide sequences are presented herein by single strand only, in the 5' to 3' direction, from left to right.

A. Antibodies

The term "antibodies" as used herein refers to all types of immunoglobulins, including IgG, IgM, IgA, IgD, and IgE. The term "immunoglobulin" includes the subtypes thereof, such as IgG$_1$, IgG$_2$, IgG$_3$, IgG$_4$, etc. Of these, IgM and IgG are preferred, and IgG is particularly preferred. The antibodies may be of any species of origin, including (for example) mouse, rat, rabbit, horse, or human, or may be chimeric antibodies. See, e.g., M. Walker et al., *Molec. Immunol.* 26, 403–11 (1989).

Monoclonal antibodies may be recombinant monoclonal antibodies produced according to the methods disclosed in Reading U.S. Pat. No. 4,474,893, or Cabilly et al., U.S. Pat. No. 4,816,567. The antibodies may also be chemically constructed by specific antibodies made according to the method disclosed in Segel et al., U.S. Pat. No. 4,676,980 (Applicants specifically intend that the disclosure of all U.S. patent references cited herein be incorporated herein by reference).

Monoclonal antibodies may be chimeric antibodies produced in accordance with known techniques. The monoclonal antibodies may be complementarity determining region-grafted antibodies (or "CDR-grafted antibodies") produced in accordance with known techniques.

The monoclonal antibody Me1-14 is known. Me1-14 is a murine antimelanoma IgG2a MAb that recognizes a high molecular weight chondroitin sulfate proteoglycan antigen of approximately 230 kDa associated with human gliomas, melanomas, and other tumors. Carrel et al., *Cancer Res.*, 40, 2523 (1980). It reacts with most melanoma cell lines as well as with a high percentage of glioma, neuroblastoma, and medulloblastoma lines. See Behnke et al., *In Brain Oncology—Biology, Diagnosis, and Therapy*, pp. 125–128 (Chatel et al., Eds. 1987); Behnke et al., *Brit. J. Neurosurg.* 2, 193, (1988); Schreyer et al., In Markers of Human Neuroectodermal Tumors, pp. 53–62 (Stall and Van Veelen, Eds. 1986); Buchegger et al., *Cancer*, 58, 655 (1986).

Antibodies employed herein are those in which the Fc fragment is deleted therefrom. Deletion of the Fc fragment may be carried out by any suitable technique, including chemical and recombinant means. Currently preferred are antibodies which comprise $F(ab')_2$ fragments of whole antibodies (in such fragments the Fc fragment is deleted). The term "$F(ab')_2$ fragment" as used herein refers to both $F(ab')_2$ fragments from IgG immunoglobulin and the corresponding fragments from immunoglobulins other than IgG. Such fragments can be produced by known techniques. The $F(ab')_2$ fragment of monoclonal antibody Me1-14 is known. See, e.g., M. Zalutsky et al., *Cancer Res.*, 50, 4105, (1990); Colapinto et al., *Cancer Res.*, 50, 1822 (1990); Behnke et al., *Brit. J. Neurosurg.* 2, 193, (1988); Behnke et al., *In Brain Oncology—Biology, Diagnosis, and Therapy*, pp. 125–128 (Chatel et al., Eds. 1987).

B. Therapeutic Antibodies

Monoclonal antibodies used for therapy (i.e., in a method of combatting cancer) may be monoclonal antibodies per se or monoclonal antibodies coupled to a therapeutic agent. Such antibodies are referred to herein as therapeutic monoclonal antibodies. Any therapeutic agent conventionally coupled to a monoclonal antibody may be employed, including (but not limited to) radioisotopes, cytotoxic agents, and chemotherapeutic agents. See generally *Monoclonal Antibodies and Cancer Therapy* (R. Reisfeld and S. Sell Eds. 1985)(Alan R. Liss Inc. NY). Therapeutic agents may be coupled to the antibody by direct means or indirect means (e.g., via a chelator), such as the Iodogen method or with N-succinimidyl-3-(tri-n-butylstanyl)benzoate (the "ATE method"), as will be apparent to those skilled in the art. See, e.g., M. Zalutsky and A. Narula, *Appl. Radiat. Isot.* 38, 1051 (1987).

Examples of radioisotopes which may be coupled to a therapeutic monoclonal antibody include, but are not limited to, $^{131}I$, $^{90}Y$, $^{211}At$, $^{212}Bi$, $^{67}Cu$, $^{186}Re$, $^{188}Re$, and $^{212}Pb$. Examples of chemotherapeutic agents which may be coupled to a therapeutic monoclonal antibody include, but are not limited to, methotrexate. Examples of cytotoxic agents which may be coupled to a therapeutic monoclonal antibody include, but are not limited to, ricin (or more particularly the ricin A chain).

It will be appreciated that monoclonal antibodies per se which are used as therapeutic monoclonal antibodies incorporate those portions of the constant region of an antibody necessary to evoke a therapeutically useful immunological response in the subject being treated.

Therapeutic monoclonal antibodies may be provided in lyophylized form in a sterile aseptic container or may be provided in a pharmaceutical formulation in combination with a pharmaceutically acceptable carrier, such as sterile pyrogen-free water or sterile pyrogen-free physiological saline solution.

C. Subjects

The method disclosed herein may be employed with subjects suspected of having solid or cystic tumors residing in the central nervous system, particularly the brain (e.g., in the cerebellum, or more preferably in the cerebral cortex, including the frontal, parietal, occipital and temporal lobes). In addition, the method disclosed herein may be employed with solid tumors residing in other solid tissue organs, such as liver, kidney, spleen, brain, breast, muscle, and prostate.

The tumor may be any tumor, primary or secondary, that binds monoclonal antibody Me1-14, including astrocytic tumors, meduloblastomas, and melanomas. Melanoma is a particularly preferred target tumor for the present invention.

The term "astrocytic tumors" as used herein is used in accordance with the World Health Organization Classification Scheme, and includes astrocytomas, anaplastic astrocytomas, and glioblastoma multiforme. See also D. Russell and L. Rubinstein, *Pathology of Tumors of the Nervous System*, pp. 83–289 (1989)(Williams and Wilkins).

Some tumors which may be treated by the method of the present invention are cystic tumors: that is, tumors which grow around a fluid-filled cavity, or cyst. Examples of such cystic tumors include (but are not limited to) cystic glioblastomas and cystic astrocytomas.

For administration, the antibody will generally be mixed, prior to administration, with a non-toxic, pharmaceutically acceptable carrier substance (e.g. normal saline or phosphate-buffered saline), and may be administered using any medically appropriate procedure, e.g., intravenous or intra-arterial administration, injection into the cerebrospinal fluid). In certain cases, intradermal, intracavity, intrathecal or direct administration to the tumor or to an artery supplying the tumor is advantageous. In addition, either intrathecal administration or injection into the carotid artery are advantageous for therapy of tumors located in the brain.

Intrathecal administration or injection may be carried out through the use of an Ommaya reservoir, in accordance with known techniques. See, e.g., F. Balis and D. Poplack, *Am J. Pediatr. Hematol. Oncol.* 11, 74, 76 FIG. 1 (1989).

Dosage of the antibody will depend, among other things, on the tumor being treated, the route of administration, the nature of the therapeutic agent employed, and the sensitivity of the tumor to the particular therapeutic agent. For example, the dosage will typically be about 1 to 10 micrograms per Kilogram subject body weight. In another example, where the therapeutic agent is $^{131}I$, the dosage to the patient will typically be from 10 mCi to 100, 300 or even 500 mCi. Stated otherwise, where the therapeutic agent is $^{131}I$, the dosage to the patient will typically be from 5,000 Rads to 100,000 Rads (preferably at least 13,000 Rads, or even at least 50,000 Rads). Doses for other radionuclides are typically selected so that the tumoricidal dose will be equivalent to the foregoing range for $^{131}$I. The antibody can be administered to the subject in a series of more than one administration, and regular periodic administration will sometimes be required.

The antibody may be administered by depositing it into the inner cavity of a cystic tumor (i.e., a fluid-filled cavity around which the tumor grows) by any suitable technique, such as by direct injection (aided by stereotaxic positioning of an injection syringe, if necessary) or by placing the tip of an Ommaya reservoir into the cavity and administering the antibody through the Ommaya reservoir. Where the tumor is a solid tumor, the antibody may be administered by first creating a resection cavity in the location of the tumor in the manner described below, and then depositing the antibody in the resection cavity in like manner as with cystic tumors.

D. Surgical Creation of an Intracranial Cystic Resection Cavity.

Virtually all cortical solitary metastases, including those appearing in the four cerebral lobes (frontal, parietal, temporal and occipital) and in the cerebellum, are amenable to creation of the cystic resection cavities by surgery, particularly those in the cerebral lobes.

The procedure differs from an ordinary craniotomy and tumor resection in only a few minor respects. First, the smallest possible cortical incision is made and the tumor is removed to the greatest extent possible by resection of tissue within the small cortical incision and in the depths of the cortex. A so-called gross total tumor resection is attempted, with the only thing prohibiting gross total resection being the potential impingement upon neurologically active areas such as speech or motor areas that would leave permanent neurologic damage if surgically approached. Following gross total resection of the tumor in a standard neurosurgical fashion with cauterization, suction, and forceps removal, the cavity is then preferably rinsed with saline until all bleeding is stopped by cauterization. Next, the pia-arachnoid membrane, which is the surface membrane lining the brain around the cortical incision, is preferably cauterized to enhance the formation of fibroblastic reaction and scarring in the pia-arachnoid area and any astroglial scarring in the areas of normal brain. The result is the formation of an enclosed, fluid-filled cavity within the brain tissue at the location from which the tumor was removed (i.e., the cavity is surrounded on all sides by the organ tissue). The enclosed nature of the resection cavity enhances retention and localization of the therapeutic agent to be administered at the desired site. If desired for administering the therapeutic agent, an Ommaya reservoir may then placed into the cavity with the tip of the catheter as deep as possible in the tumor bed, and the reservoir secured to the bone in accordance with standard techniques. A standard water-tight dural closure may then be carried out with sutures, as in any other craniotomy.

Resection cavities are formed in other solid tissue organs, as described above, by modification of the foregoing techniques which will be apparent to those skilled in the art.

The following examples are provided to illustrate the present invention, and should not be construed as limiting thereof. In these examples, ml means milliliter, ng means nanograms, μg means microgram, mg means milligram, g means gram, nm means nanometers, mCI means millicurie, kb means kilobase, v/v means volume to volume, M means Molar, mM means millimolar, N means normal, ° C. means degrees Centigrade, h means hour, and cpm means counts per minute.

EXAMPLE 1

Drug Formulation

Drug is formulated as 2 ml of a sterile, pyrogen-free solution that contains 10 mg of monoclonal antibody ME1-14 F(ab')$_2$ fragments, 40–80 mCi $^{131}$I, 0.7 to 0.9% sodium chloride, 0–0.6% sodium phosphate, 0.5% albutein, and water. Antibody is conjugated to $^{131}$I by the Iodogen method in accordance with known techniques. See, e.g., Colapinto et al., *Cancer Res.* 50, 1822 (1990).

EXAMPLE 2

Intrathecal Administration of ME1-14 F(ab')$_2$ to a Melanoma Patient

A 60 year old adult male with an intracranial melanoma was administered 54.5 mCi of $^{131}$I conjugated to 9.2 mg of monoclonal antibody ME1-14 F(ab')$_2$ by the Iodogen method and formulated as described above through an Ommaya reservoir placed into the lateral ventricle of the brain. Examination of CSF after treatment indicated a partial response; clinical examination after treatment indicated disease stabilization. The patient survived 6 months beyond treatment.

EXAMPLE 3

Intrathecal Administration of ME1-14 F(ab')$_2$ to a Melanoma Patient

A 26 year old adult female with an intracranial melanoma was administered 41.7 mCi of $^{131}$I conjugated to 10.2 mg of monoclonal antibody ME1-14 F(ab')$_2$ by the Iodogen method through an Ommaya reservoir placed into the lateral ventricle of the brain. Examination of CSF and clinical examination after treatment indicated progressive disease. The patient survived 1 month beyond treatment.

EXAMPLE 4

Intrathecal Administration of ME1-14 F(ab')$_2$ to a Melanosis Patient

A 10 year old female with melanosis was administered 40.0 mCi of $^{131}$I conjugated to 9.8 mg of monoclonal antibody ME1-14 F(ab')$_2$ by the Iodogen method through an Ommaya reservoir placed into the lateral ventricle of the brain. Clinical examination after treatment indicated disease stabilization. The patient survived 4 months beyond treatment.

EXAMPLE 5

Intrathecal Administration of ME1-14 F (ab')$_2$ to a Melanoma Patient

A 55 year old adult female with an intracranial melanoma was administered 44.0 mCi of $^{131}$I conjugated to 9.0 mg of monoclonal antibody ME1-14 F(ab')$_2$ by the Iodogen method through an Ommaya reservoir placed into the lateral ventricle of the brain. Examination of CSF after treatment indicated a partial response, and clinical examination after treatment indicated disease stabilization. The patient survived 2.75 months beyond treatment.

EXAMPLE 6

Intrathecal Administration of ME1-14 F(ab')$_2$ to a Melanoma Patient

A 69 year old adult female with an intracranial melanoma was administered 46.0 mCi of $^{131}$I conjugated to 7.7 mg of monoclonal antibody ME1-14 F(ab')$_2$ by the Iodogen method through an Ommaya reservoir placed into the lateral ventricle of the brain. Examination of CSF and clinical examination after treatment indicated disease stabilization. The patient survived 4 months beyond treatment.

EXAMPLE 7

Intratheoal Administration of ME1-14 F(ab')$_2$ to a Melanoma Patient

A 48 year old adult male with an intracranial melanoma was administered 60.0 mCi of $^{131}$I conjugated to 10.0 mg of monoclonal antibody ME1-14 F(ab')$_2$ by the Iodogen method through an Ommaya reservoir placed into the lateral ventricle of the brain. Examination of CSF after treatment indicated a partial response. Clinical and radiographic examination after treatment indicated a partial response. The patient survived 6 months beyond treatment.

EXAMPLE 8

Intrathecal Administration of ME1-14 F(ab')$_2$ to a Melanoma Patient

A 38 year old adult female with an intracranial melanoma was administered 60.0 mCi of $^{131}$I conjugated to 10.0 mg of monoclonal antibody ME1-14 F(ab')$_2$ by the Iodogen method through an Ommaya reservoir placed into the lateral ventricle of the brain. Examination of CSF after treatment indicated a complete response, and clinical examination after treatment also indicated a complete response. The patient is alive at 8 months post treatment.

EXAMPLE 9

Intrathecal Administration of ME1-14 F(ab')$_2$ to a Melanoma Patient

A 26 year old adult female with an intracranial melanoma was administered 59.8 mCi of $^{131}$I conjugated to 10.0 mg of monoclonal antibody ME1-14 F(ab')$_2$ by the Iodogen method through an Ommaya reservoir placed into the lateral ventricle of the brain. The patient is alive at 3 months post-treatment. No conclusions can be drawn from post treatment examinations at this early date.

EXAMPLE 10

Surgical Creation of an Intracranial Cystic Resection Cavity in a Human Melanoma Patient A cystic resection cavity was surgically created in a 37 year old male patient afflicted with an intracranial melanoma. The procedure was carried out in essentially the same manner as an ordinary craniotomy and tumor resection, but differed in a few respects. First, the smallest possible cortical incision was made and the tumor was removed to the greatest extent possible by resection of tissue within the small cortical incision and in the depths of the cortex. A so-called gross total tumor resection was attempted, with the only thing prohibiting gross total resection being the potential impingement upon neurologically active areas such as speech or motor areas that would leave permanent neurologic damage if surgically approached. Following gross total resection of the tumor in a standard neurosurgical fashion with cauterization, suction, and forceps removal, the cavity was then rinsed with saline until all bleeding was stopped by cauterization and the pia-arachnoid membrane, which is the surface membrane lining the brain around the cortical incision, was cauterized to enhance the formation of fibroblastic reaction and scarring in the pia-arachnoid area and any astroglial scarring in the areas of normal brain. An Ommaya reservoir was then placed into the cavity with the tip of the catheter as deep as possible in the tumor bed, and the reservoir secured to the bone in accordance with standard techniques. A standard water-tight dural closure was then carried out with sutures.

EXAMPLE 11

Administration of ME1-14 F(ab')$_2$ to an Intracranial Cystic Resection Cavity in a Human Melanoma Patient The patient described in example 10 was administered 37.0 mCi of $^{131}$I conjugated to 10 mg of monoclonal antibody ME1-14 F(ab')$_2$ by the Iodogen method through an Ommaya reservoir placed into the cystic resection cavity created as described above. One month after administration, the patient is still alive.

Technetium albumin injections of the cystic resection cavity, followed by sequential radionuclide scans of the brain, showed up to approximately 90% retention of the injected radionuclide albumin conjugate for 72 hours after injection and significant retention of the therapeutic dose of radiolabeled antibody to give a radiation dose calculated to range between 20,000 and 60,000 rads to the walls of the cyst.

EXAMPLE 12

Cloning and Expression of a Mouse/human Chimerio Antibody Cross-reactive with ME1-14

This example describes the molecular cloning and characterization of variable region genes for ME1-14 antibody. Rearranged immunoglobulin genes from ME1-14 hybridoma were identified on Southern blot analysis. Putative rearranged light- and heavy-chain genes were cloned from λ-Zap11 Me1-14 genomic libraries and were sequenced for nucleotide analysis. One of the putative heavy-chain EcoR1 fragments (3.5 kb) had all the features of an intact variable region, including a functional leader sequence, in-frame V-D and D-J junctions, and cysteines 22 and 92. The gene had considerable homology with the mouse heavy-chain subgroup 111B gene. Like the heavy-chain gene, one of the rearranged K-chain HindIII fragments (4 kb) for Me1-14 had all of the characteristics of the functional variable region and showed considerable homology to K-chain group V. The variable region genes for heavy and light chains were linked to human constant region exons in the expression vectors at the unique sites and cotransfected into SP2/0 cells, and stable integration and expression was obtained. The chimeric antibody exhibited the same specificity and affinity as that of the murine ME1-14, but production in culture medium supernatants was clonally variable. Ascites production of SP2/0 transfectants was sufficiently high (850 µg/ml).

The nucleotide sequence and deduced amino acid sequence for the Me1-14 heavy-chain variable region is given in FIG. 1a, and the nucleotide sequence and deduced amino acid sequence for the Me1-14 light chain variable region is given in FIG. 1b. These data are useful for the identification of other antibodies which bind to the epitope bound by monoclonal antibody ME1-14.

The foregoing examples are illustrative of the present invention, and are not to be construed as limiting thereof. The invention is defined by the following claims, with equivalents of the claims to be included therein.

That which is claimed is:

1. A method of treating a cystic brain tumor in a human subject comprising:

administering to a human subject afflicted with a cystic brain tumor an antibody in a therapeutically effective amount, wherein the Fc fragment of said antibody is deleted, wherein said antibody is selected from the group consisting of monoclonal antibody Me1-14 having the amino acid sequence given in SEQ ID NO: 2 and SEQ ID NO: 4, and antibodies that specifically bind to the epitope specifically bound by monoclonal antibody Me1-14, wherein said cystic brain tumor binds monoclonal antibody Me1-14;

and wherein said administering step is carried out by depositing said antibody in the cyst cavity of said cystic brain tumor.

2. A method according to claim 1, wherein said tumor is an astrocytic tumor.

3. A method according to claim 1, wherein said tumor is a melanoma.

4. A method according to claim 1, wherein said tumor is a medulloblastoma.

5. A method according to claim 1 wherein said antibody is coupled to a therapeutic agent, said therapeutic agent selected from the group consisting of radioisotopes, cytotoxic agents, and chemotherapeutic agents.

6. A method according to claim 1 wherein said antibody is coupled to a radioisotope.

7. A method according to claim 6 wherein said radioisotope is selected from the group consisting of $^{131}$I, $^{90}$Y, $^{211}$At, $^{212}$Bi, $^{67}$Cu, $^{186}$Re, $^{188}$Re, and $^{212}$Pb.

8. A method according to claim 7 wherein said antibody is coupled to $^{131}$I.

9. A method according to claim 6 wherein said antibody coupled to a radioisotope is administered in an amount of from 5,000 rads to 100,000 rads.

10. A method of treating a tumor in the central nervous system (CNS) of a human subject, comprising:

administering to a human subject carrying a tumor in the CNS a monoclonal antibody Me1-14 F(ab')$_2$ fragment having the amino acid sequence given in SEQ ID NO: 2 and SEQ ID NO: 4, coupled to $^{131}$I in a therapeutically effective amount, wherein said tumor binds monoclonal antibody Me1-14;

wherein said administering step is carried out by intrathecal injection.

11. A method according to claim 10, and which antibody is administered in an amount of from 5,000 rads to 100,000 rads.

12. A method of treating a solid tumor in a human subject in need of such treatment, comprising:

removing a solid tumor from a solid tissue organ of an afflicted human subject; then forming an enclosed resection cavity in said solid tissue organ at the location from which said solid tumor was removed; and then administering to said subject an antibody in a therapeutically effective amount, wherein said solid tumor binds monoclonal antibody Me1-14;

wherein said antibody is selected from the group consisting of monoclonal antibody Me1-14 having the amino acid sequence given in SEQ ID NO: 2 and SEQ ID NO: 4, and antibodies that specifically bind to the epitope specifically bound by monoclonal antibody Me1-14, and wherein the Fc fragment of said antibody is deleted;

and wherein said administering step is carried out by depositing said antibody in said resection cavity.

13. A method according to claim 12, wherein said organ is selected from the group consisting of liver, kidney, spleen, breast, muscle, and prostate.

14. A method according to claim 12, wherein said organ is the brain.

15. A method according to claim 12, wherein said tumor is an astrocytic tumor.

16. A method according to claim 12, wherein said tumor is a melanoma.

17. A method according to claim 12, wherein said tumor is a medulloblastoma.

18. A method according to claim 12, wherein said antibody is coupled to a therapeutic agent, said therapeutic agent selected from the group consisting of radioisotopes, cytotoxic agents, and chemotherapeutic agents.

19. A method according to claim 12 wherein said antibody is coupled to a radioisotope.

20. A method according to claim 19 wherein said radioisotope is selected from the group consisting of $^{131}I$, $^{90}Y$, $^{211}At$, $^{212}Bi$, $^{67}Cu$, $^{186}Re$, $^{188}Re$, and $^{212}Pb$.

21. A method according to claim 19 wherein said antibody is coupled to $^{131}I$.

22. A method according to claim 19 wherein said antibody coupled to a radioisotope is administered in an amount of from 5,000 rads to 100,000 rads.

23. A method according to claim 12, wherein said administering step is carried out by injection.

24. A method of treating a solid melanoma tumor in the brain of a human subject in need of such treatment, comprising:

removing a solid melanoma tumor from the brain of an afflicted human subject; then forming an enclosed resection cavity in the brain of said subject at the location from which said solid tumor was removed; and then administering to said subject a monoclonal antibody Me1-14 F(ab')$_2$ fragment having the amino acid sequence given in SEQ ID NO: 2 and SEQ ID NO: 4, coupled to $^{131}I$ in a therapeutically effective amount, wherein said solid melanoma binds monoclonal antibody Me1-14;

wherein said administering step is carried out by depositing said antibody fragment in said resection cavity.

25. A method according to claim 24 wherein said antibody is administered in an amount of from 5,000 rads to 100,000 rads.

26. A method according to claim 24, wherein said administering step is carried out by injection.

27. A method according to claim 10 wherein said tumor is selected from the group consisting of melanomas, astrocytic tumors, and medulloblastomas.

28. A method according to claim 10 wherein said tumor is a melanoma.

* * * * *

UNITED STATES PATENT AND TRADEMARK OFFICE
CERTIFICATE OF CORRECTION
5,558,852

PATENT NO. :
DATED : 24 September 1996
INVENTOR(S) : Darrell, D. Bigner, Michael R. Zalutsky, Stefan Carrel It is certified that error appears in the above-indentified patent and that said Letters Patent is hereby corrected as shown below:

Title page, item [54] and col. 1, line 1-3,

Please correct title per Examiner's Paper #36 from "METHODS OF TREATING MELANOMAS AND GLIOMAS WITH MONOCLONAL ANTIBODY ME1-14" to read --METHODS OF TREATING TUMORS WITH MONOCLONAL ANTIBODY ME1-14--.

Please add --Stefan Carrel, St. Regies, Switzerland-- to Inventors:

Column 2, line 42, please correct "(SEQ ID NO:1 and SEQ ID NO:1, RESPECTIVELY) to read --(SEQ ID NO:1 and SEQ ID NO:2, RESPECTIVELY)--.

Column 7, line 15, please correct "Intratheoal" to read --Intrathecal--.

Column 8, line 44, please correct "Chimerio" to read --Chimeric--.

Signed and Sealed this

Eleventh Day of February, 1997

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 519 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 157..519

( x i ) SEQUENCE DESCRIPTION: SEQ ID NO:1:

```
CTTCTTATGA ACTTCGGGTT CAGCTTGATT TTCCTTGTCC TTGTTTTAAA AGGTAATTTA        60

TTGAGAAGAG ATGACATCTA TTTTACGCAC ATGAGACAGA AAAAATGTGG TTTGTTTTGT       120

TAGTGACAGT TTTCCAACCA GTATTCTCTG TTTGTA GGT GTC CAG TGT GAA GTG         174
                                      Gly Val Gln Cys Glu Val
                                       1               5

AAG CTG GTG GAG TCT GGG GGA GGC TTA GTG AAG CCT GGA GGG TCC CTG         222
Lys Leu Val Glu Ser Gly Gly Gly Leu Val Lys Pro Gly Gly Ser Leu
             10                  15                  20

AAA CTC TCC TGT GCA GCC TCT GGA TTC ACT TTC AGT AGC TAT GCC ATG         270
Lys Leu Ser Cys Ala Ala Ser Gly Phe Thr Phe Ser Ser Tyr Ala Met
         25                  30                  35

TCT TGG GTT CGC CAG ACT CCA GAG AAG AGC CTG GAG TGG GTC GCA TCC         318
Ser Trp Val Arg Gln Thr Pro Glu Lys Ser Leu Glu Trp Val Ala Ser
     40                  45                  50

ATT AGT AGT GGT GAT AGC ACC TAC TAT CCA GAC AGT GTG AAG GGC CGA         366
Ile Ser Ser Gly Asp Ser Thr Tyr Tyr Pro Asp Ser Val Lys Gly Arg
 55                  60                  65                  70

TTC ACC ATC TCC AGA GAT AAT GCC AGG AAC ATC CTC TAC CTG CAA ATG         414
Phe Thr Ile Ser Arg Asp Asn Ala Arg Asn Ile Leu Tyr Leu Gln Met
                 75                  80                  85

AGC AGT CTG AGG TCT GAG GAC ACG GCC ATG TAT TAC TGT GCA AGA GGC         462
Ser Ser Leu Arg Ser Glu Asp Thr Ala Met Tyr Tyr Cys Ala Arg Gly
             90                  95                 100

GGA TGG TTA CAC TAC TTT GAC TAC GGG GGC CAA GGC ACC ACT CTC ACA         510
Gly Trp Leu His Tyr Phe Asp Tyr Gly Gly Gln Gly Thr Thr Leu Thr
            105                 110                 115

GTC TCC TCA                                                             519
Val Ser Ser
        120
```

( 2 ) INFORMATION FOR SEQ ID NO:2:

( i ) SEQUENCE CHARACTERISTICS:
        ( A ) LENGTH: 121 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Gly | Val | Gln | Cys | Glu | Val | Lys | Leu | Val | Glu | Ser | Gly | Gly | Gly | Leu | Val |
|---|---|---|---|---|---|---|---|---|---|---|---|---|---|---|---|
| 1 | | | | 5 | | | | | 10 | | | | | 15 | |

| Lys | Pro | Gly | Gly | Ser | Leu | Lys | Leu | Ser | Cys | Ala | Ala | Ser | Gly | Phe | Thr |
|---|---|---|---|---|---|---|---|---|---|---|---|---|---|---|---|
| | | | 20 | | | | | 25 | | | | | 30 | | |

| Phe | Ser | Ser | Tyr | Ala | Met | Ser | Trp | Val | Arg | Gln | Thr | Pro | Glu | Lys | Ser |
|---|---|---|---|---|---|---|---|---|---|---|---|---|---|---|---|
| | | 35 | | | | | 40 | | | | | 45 | | | |

| Leu | Glu | Trp | Val | Ala | Ser | Ile | Ser | Ser | Gly | Asp | Ser | Thr | Tyr | Tyr | Pro |
|---|---|---|---|---|---|---|---|---|---|---|---|---|---|---|---|
| | 50 | | | | | 55 | | | | | 60 | | | | |

| Asp | Ser | Val | Lys | Gly | Arg | Phe | Thr | Ile | Ser | Arg | Asp | Asn | Ala | Arg | Asn |
|---|---|---|---|---|---|---|---|---|---|---|---|---|---|---|---|
| 65 | | | | | 70 | | | | | 75 | | | | | 80 |

| Ile | Leu | Tyr | Leu | Gln | Met | Ser | Ser | Leu | Arg | Ser | Glu | Asp | Thr | Ala | Met |
|---|---|---|---|---|---|---|---|---|---|---|---|---|---|---|---|
| | | | | 85 | | | | | 90 | | | | | 95 | |

| Tyr | Tyr | Cys | Ala | Arg | Gly | Gly | Trp | Leu | His | Tyr | Phe | Asp | Tyr | Gly | Gly |
|---|---|---|---|---|---|---|---|---|---|---|---|---|---|---|---|
| | | | 100 | | | | | 105 | | | | | 110 | | |

| Gln | Gly | Thr | Thr | Leu | Thr | Val | Ser | Ser |
|---|---|---|---|---|---|---|---|---|
| | | 115 | | | | | 120 | |

( 2 ) INFORMATION FOR SEQ ID NO:3:

( i ) SEQUENCE CHARACTERISTICS:
        ( A ) LENGTH: 599 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: join(80..127, 249..584)

( x i ) SEQUENCE DESCRIPTION: SEQ ID NO:3:

```
ATATTCTACT GCCCCAGAGA TTTAATAATC TGATCATACA CACTCCAACA GTCATTCTTG           60

GTCAGGAGAC GTTGTAGAA ATG AGA CCG TCT ATT CAG TTC CTG GGG CTC TTG          112
                     Met Arg Pro Ser Ile Gln Phe Leu Gly Leu Leu
                       1               5                      10

TTG TTC TGG CTT CAT GGTAAGGAGT TTAACATTGA ATATGCTAAA AAGAGTATGT           167
Leu Phe Trp Leu His
               15

GATCAGGAAT TTCTGGTCCT TCAGAAAAAT CTTCTTTGAA TATAATTAAT TTCATAGGGA         227

CTTGTGTTCT TTTTAATTAT A GGT GCT CAC TGT GAC ATC CAG ATG ACA CAG           278
                       Gly Ala His Cys Asp Ile Gln Met Thr Gln
                                   20                      25

TCT CCA TCC TCA CTG TCT GCA TCT CTG GGA GGC AAG GTC ACC ATC ACT           326
Ser Pro Ser Ser Leu Ser Ala Ser Leu Gly Gly Lys Val Thr Ile Thr
                30                  35                  40

TGC AAG GCA AGC CAA GAC ATT AAC AAG TAT ATA GCT TGG TAT CAA CAC           374
Cys Lys Ala Ser Gln Asp Ile Asn Lys Tyr Ile Ala Trp Tyr Gln His
            45                  50                  55

AAA CCT GGA AAA GGT CCT AGG CTG CTC ATG CAT TAC ACA TCT ACA TTA           422
Lys Pro Gly Lys Gly Pro Arg Leu Leu Met His Tyr Thr Ser Thr Leu
        60                  65                  70

CAG CCA GGC ATC CCA TCA AGG TTC AGT GGA AGT GGG TCT GGG AGA GAT           470
Gln Pro Gly Ile Pro Ser Arg Phe Ser Gly Ser Gly Ser Gly Arg Asp
75                  80                  85                  90

TAT TCC TTC AGC ATC AGC AAC CTG GAG CCT GAA GAT ATT GCA ACT TAT           518
Tyr Ser Phe Ser Ile Ser Asn Leu Glu Pro Glu Asp Ile Ala Thr Tyr
```

5,558,852

-continued

|  |  |  |  |  |  | 95 |  |  |  |  |  | 100 |  |  |  |  | 105 |  |  |  |
|---|---|---|---|---|---|---|---|---|---|---|---|---|---|---|---|---|---|---|---|---|
| TAT | TGT | CTA | CAG | TAT | GAT | AAT | CTT | CTC | ACG | TTC | GGA | GGG | GGG | ACC | AAG |  |  |  |  | 566 |
| Tyr | Cys | Leu | Gln | Tyr | Asp | Asn | Leu | Leu | Thr | Phe | Gly | Gly | Gly | Thr | Lys |  |  |  |  |  |
|  |  |  | 110 |  |  |  |  | 115 |  |  |  |  | 120 |  |  |  |  |  |  |  |

| CTG | GAA | ATA | AAA | CGT | AAG | TAGTCTTCTC | AACTT |  | 599 |
|---|---|---|---|---|---|---|---|---|---|
| Leu | Glu | Ile | Lys | Arg | Lys |  |  |  |  |
|  |  | 125 |  |  |  |  |  |  |  |

( 2 ) INFORMATION FOR SEQ ID NO:4:

( i ) SEQUENCE CHARACTERISTICS:
        ( A ) LENGTH: 128 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Arg | Pro | Ser | Ile | Gln | Phe | Leu | Gly | Leu | Leu | Leu | Phe | Trp | Leu | His |
|---|---|---|---|---|---|---|---|---|---|---|---|---|---|---|---|
| 1 |  |  |  | 5 |  |  |  |  | 10 |  |  |  |  | 15 |  |

| Gly | Ala | His | Cys | Asp | Ile | Gln | Met | Thr | Gln | Ser | Pro | Ser | Ser | Leu | Ser |
|---|---|---|---|---|---|---|---|---|---|---|---|---|---|---|---|
|  |  |  | 20 |  |  |  |  | 25 |  |  |  |  | 30 |  |  |

| Ala | Ser | Leu | Gly | Gly | Lys | Val | Thr | Ile | Thr | Cys | Lys | Ala | Ser | Gln | Asp |
|---|---|---|---|---|---|---|---|---|---|---|---|---|---|---|---|
|  |  | 35 |  |  |  |  | 40 |  |  |  |  | 45 |  |  |  |

| Ile | Asn | Lys | Tyr | Ile | Ala | Trp | Tyr | Gln | His | Lys | Pro | Gly | Lys | Gly | Pro |
|---|---|---|---|---|---|---|---|---|---|---|---|---|---|---|---|
|  | 50 |  |  |  |  | 55 |  |  |  |  | 60 |  |  |  |  |

| Arg | Leu | Leu | Met | His | Tyr | Thr | Ser | Thr | Leu | Gln | Pro | Gly | Ile | Pro | Ser |
|---|---|---|---|---|---|---|---|---|---|---|---|---|---|---|---|
| 65 |  |  |  |  | 70 |  |  |  |  | 75 |  |  |  |  | 80 |

| Arg | Phe | Ser | Gly | Ser | Gly | Ser | Gly | Arg | Asp | Tyr | Ser | Phe | Ser | Ile | Ser |
|---|---|---|---|---|---|---|---|---|---|---|---|---|---|---|---|
|  |  |  |  | 85 |  |  |  |  | 90 |  |  |  |  | 95 |  |

| Asn | Leu | Glu | Pro | Glu | Asp | Ile | Ala | Thr | Tyr | Tyr | Cys | Leu | Gln | Tyr | Asp |
|---|---|---|---|---|---|---|---|---|---|---|---|---|---|---|---|
|  |  |  | 100 |  |  |  |  | 105 |  |  |  |  | 110 |  |  |

| Asn | Leu | Leu | Thr | Phe | Gly | Gly | Gly | Thr | Lys | Leu | Glu | Ile | Lys | Arg | Lys |
|---|---|---|---|---|---|---|---|---|---|---|---|---|---|---|---|
|  |  | 115 |  |  |  |  | 120 |  |  |  |  | 125 |  |  |  |